US007381540B2

(12) United States Patent
Kitabayashi et al.

(10) Patent No.: US 7,381,540 B2
(45) Date of Patent: Jun. 3, 2008

(54) COMPOSITION FOR MEASURING GLUCOSE HAVING IMPROVED SUBSTRATE SPECIFICITY

(75) Inventors: Masao Kitabayashi, Tsuruga (JP); Hiroshi Aiba, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 11/393,285

(22) Filed: Mar. 30, 2006

(65) Prior Publication Data

US 2007/0037239 A1 Feb. 15, 2007

(30) Foreign Application Priority Data

Aug. 11, 2005 (JP) ............................ 2005-233047
Oct. 26, 2005 (JP) ............................ 2005-311074

(51) Int. Cl.
*C12Q 1/32* (2006.01)
(52) U.S. Cl. ........................................................ 435/26
(58) Field of Classification Search ..................... None
See application file for complete search history.

(56) References Cited

U.S. PATENT DOCUMENTS 6,773,564 B1 * 8/2004 Yugawa et al. ........ 204/403.14
2006/0073580 A1 4/2006 Sode

FOREIGN PATENT DOCUMENTS

EP 1 666 586 A1 6/2006
JP 11-243949 A 9/1999
WO WO 02/08763 A2 1/2002
WO WO 02/34919 A1 5/2002
WO WO 03/106668 A1 12/2003
WO WO 2005/026340 A1 3/2005

OTHER PUBLICATIONS

Cleton-Jansen et al. Mol Gen Genet 1991;229:206-212.*
Igarashi et al. Biochem and Biophysical Res Communications 1999:264:820-824.*
European Patent Office, Extended European Search Report in counterpart European Patent Application No. 06006805.3 (Nov. 16, 2006).

* cited by examiner

*Primary Examiner*—Jon P Weber
*Assistant Examiner*—Bin Shen
(74) *Attorney, Agent, or Firm*—Leydig, Voit & Mayer, Ltd.

(57) ABSTRACT

The present invention relates to a method for lowering activity with respect to maltose in glucose measurement comprising a step of reacting modified pyrroloquinoline quinone dependent glucose dehydrogenase subjected to amino acid sequence modification, wherein pyrroloquinoline quinone dependent glucose dehydrogenase is reacted in the presence of at least one type of substance selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

11 Claims, 2 Drawing Sheets

Fig. 1

[92.3% / 480 aa] INT/OPT.Score : < 1367/ 2198 >

```
  1' MNKHLLAKIT LLGAAQLFTF HTAFADIPLT PAQFAKAKTE NFDKKVILSN LNKPHALLWG
     *********. **.*.** *.  .****.*** *.******.* ********** **********
  1" MNKHLLAKIA LLSAVQLVTL -SAFADVPLT PSQFAKAKSE NFDKKVILSN LNKPHALLWG

 61' PDNQIWLTER ATGKILRVNP VSGSAKTVFQ VPEIVSDADG QNGLLGFAFH PDFKHNPYIY
     ********** **********  ***.***** *****.**** ********** ****.*****
 60" PDNQIWLTER ATGKILRVNP ESGSVKTVFQ VPEIVNDADG QNGLLGFAFH PDFKNNPYIY

121' ISGTFKNPKS TDKELPNQTI IRRYTYNKTT DTFEKPIDLI AGLPSSKDHQ SGRLVIGPDQ
     ********** ********** ********.* **.***.**. ********** **********
120" ISGTFKNPKS TDKELPNQTI IRRYTYNKST DTLEKPVDLL AGLPSSKDHQ SGRLVIGPDQ

181' KIYYTIGDQG RNQLAYLFLP NQAQHTPTQQ ELNSKDYHTY MGKVLRLNLD GSVPKDNPSF
     ********** ********** ********** ***.****** ********** **.*******
180" KIYYTIGDQG RNQLAYLFLP NQAQHTPTQQ ELNGKDYHTY MGKVLRLNLD GSIPKDNPSF

241' NGVVSHIYTL GHRNPQGLAF APNGKLLQSE QGPNSDDEIN LVLKGGNYGW PNVAGYKDDS
     ********** ********** .********* ********** *..******* **********
240" NGVVSHIYTL GHRNPQGLAF TPNGKLLQSE QGPNSDDEIN LIVKGGNYGW PNVAGYKDDS

301' GYAYANYSAA TNKSQIKDLA QNGIKVATGV PVTKESEWTG KNFVPPLKTL YTVQDTYNYN
     ********** .*** ***** ***.***.** ********** ********** **********
300" GYAYANYSAA ANKS-IKDLA QNGVKVAAGV PVTKESEWTG KNFVPPLKTL YTVQDTYNYN

361' DPTCGEMAYI CWPTVAPSSA YVYTGGKKAI PGWENTLLVP SLKRGVIFRI KLDPTYSTTL
     *******.** ********** ***.****** .********* ********** *********
359" DPTCGEMTYI CWPTVAPSSA YVYKGGKKAI TGWENTLLVP SLKRGVIFRI KLDPTYSTTY

421' DDAIPMFKSN NRYRDVIASP EGNTLYVLTD TAGNVQKDDG SVTHTLENPG SLIKFTYNGK   (SEQ ID NO: 3)
     ***.****** ********** .**.****** ********** ***.****** *******..*
419" DDAVPMFKSN NRYRDVIASP DGNVLYVLTD TAGNVQKDDG SVTNTLENPG SLIKFTYKAK   (SEQ ID NO: 4)
```

Fig. 2

[91.3% / 480 aa] INT/OPT.Score : < 2221/ 2228 >

```
  1' MNKHLLAKIT LLGAAQLFTF HTAFADIPLT PAQFAKAKTE NFDKKVILSN LNKPHALLWG
     ********** *******.*. ..****.*** *.******** .*****.*** **********
  1" MNKHLLAKIT LLGAAQLLTL NSAFADVPLT PSQFAKAKTE SFDKKVLLSN LNKPHALLWG

 61' PDNQIWLTER ATGKILRVNP VSGSAKTVFQ VPEIVSDADG QNGLLGFAFH PDFKHNPYIY
     ********** **********  ***.***** *****.**** ********** ****.*****
 61" PDNQIWLTER ATGKILRVNP ESGSVKTVFQ VPEIVNDADG QNGLLGFAFH PDFKNNPYIY

121' ISGTFKNPKS TDKELPNQTI IRRYTYNKTT DTFEKPIDLI AGLPSSKDHQ SGRLVIGPDQ
      ********* ********** ********.* **.***.**. ********** **********
121" VSGTFKNPKS TDKELPNQTI IRRYTYNKAT DTLEKPVDLL AGLPSSKDHQ SGRLVIGPDQ

181' KIYYTIGDQG RNQLAYLFLP NQAQHTPTQQ ELNSKDYHTY MGKVLRLNLD GSVPKDNPSF
     ********** ********** ********** **..****** ********** **.*******
181" KIYYTIGDQG RNQLAYLFLP NQAQHTPTQQ ELSGKDYHTY MGKVLRLNLD GSIPKDNPSF

241' NGVVSHIYTL GHRNPQGLAF APNGKLLQSE QGPNSDDEIN LVLKGGNYGW PNVAGYKDDS
     ***.****** ********** .********* ********** *..******* **********
241" NGVISHIYTL GHRNPQGLAF TPNGKLLQSE QGPNSDDEIN LIVKGGNYGW PNVAGYKDDS

301' GYAYANYSAA TNKSQIKDLA QNGIKVATGV PVTKESEWTG KNFVPPLKTL YTVQDTYNYN
     ********** .**.*****.  ***.***.** ********** ********** **********
301" GYAYANYSAA SNKAQIKDLG QNGLKVAAGV PVTKESEWTG KNFVPPLKTL YTVQDTYNYN

361' DPTCGEMAYI CWPTVAPSSA YVYTGGKKAI PGWENTLLVP SLKRGVIFRI KLDPTYSTTL
     *****.*.** ********** ***.****** .********* ********** *******.*
361" DPTCGDMTYI CWPTVAPSSA YVYKGGKKAI SGWENTLLVP SLKRGVIFRI KLDPTYSATY

421' DDAIPMFKSN NRYRDVIASP EGNTLYVLTD TAGNVQKDDG SVTHTLENPG SLIKFTYNGK   (SEQ ID NO: 5)
     ***.****** ********** .**.****** *.******** ***.****** *******..*
421" DDAVPMFKSN NRYRDVIASP DGNVLYVLTD TSGNVQKDDG SVTNTLENPG SLIKFTYKAK   (SEQ ID NO: 6)
```

COMPOSITION FOR MEASURING GLUCOSE HAVING IMPROVED SUBSTRATE SPECIFICITY

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: 22,788 bytes ASCII (Text) file named "AmendedSequenceListing," created on Jun. 25, 2007.

FIELD OF THE INVENTION

The present invention relates to a method for lowering activity for maltose in glucose measurement comprising the step of reacting modified pyrroloquinoline quinone dependent glucose dehydrogenase having a modification in the amino acid sequence (hereinafter, pyrroloquinoline quinone is referred to as "PQQ", glucose dehydrogenase is referred to as "GDH", and pyrroloquinoline quinone dependent glucose dehydrogenase is referred to as "PQQGDH", respectively), a glucose measurement composition wherein activity for maltose is lowered, a glucose sensor and methods for production thereof.

BACKGROUND ART

PQQGDH is glucose dehydrogenase (GDH) using pyrroloquinoline quinone as a coenzyme, and can be used for assay of blood glucose because it catalyzes a reaction in which glucose is oxidized to produce gluconolactone. A glucose concentration in blood is a very important indicator as an important marker for diabetes in clinical diagnosis. Although measurement of blood glucose concentration is currently mainly performed by methods using a biosensor that uses glucose oxidase, since the reaction is affected by dissolved oxygen concentration, there was the possibility of the occurrence of error in the measured values. PQQ dependent glucose dehydrogenase has attracted attention as a new alternative enzyme to glucose oxidase.

Our group found that *Acinetobacter baumannii* strain NCIMB11517 produces PQQGDH, and constructed a gene cloning and high expression system (see, for example, Japanese Patent Application Laid-open No. H11-243949). However, this wild type of PQQGDH had problems with activity with respect to sugar other than glucose (i.e., substrate specificity), and with respect to maltose in particular, as compared with glucose oxidase.

DISCLOSURE OF THE INVENTION

PQQGDH catalyzes a reaction in which D-glucose is oxidized to produce D-glucono-1,5-lactone. PQQGDH is not influenced by dissolved oxygen, and has an enzymatic property of no coenzyme requirement. PQQGDH is expected to apply a variety of applications such as biological diagnostics to assay blood glucose level, and blood glucose sensor. It is also noted that PQQGDH has a problem with respect to substrate specificity, such as acting on disaccharides, in particular maltose.

The inventors made an extensive research on the cause of the problems to be solved and found that PQQGDH had a low reactivity on ferricyanide ion usually used as a mediator in blood glucose sensor.

The inventors further investigated and demonstrated that the low reactivity on ferricyanide ion was caused by the influence of near neutral buffer conditions leading to a substrate specificity of enzymatic reaction.

WO03/106668 discloses a means to improve the substrate specificity of PQQGDH, wherein PQQGDH gene is modified. However, WO03/106668 does not disclose or suggest a means to solve the problem of substrate specificity other than glucose, in particular maltose.

Therefore, as a result of conducting extensive studies on improvements from other perspectives in parallel with modification by genetic engineering techniques, the inventors of the present invention found that substrate specificity is improved by examining compositions other than modified PQQGDH in a method for measuring glucose that contains a step that reacts an modified PQQGDH subjected to substitution, insertion, deletion or other modification of the amino acid sequence, thereby leading to filing of the present application.

More specifically, the present invention is composed by optimizing substances contained in the composition and/or pH conditions.

Namely, the present invention is composed of the composition described below.

[Item 1] A method for lowering a reactivity on maltose in glucose measurement comprising a step of reacting modified pyrroloquinoline quinone dependent glucose dehydrogenase subjected to amino acid sequence modification, wherein pyrroloquinoline quinone dependent glucose dehydrogenase is reacted in the presence of at least one substance selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

[Item 2] The method according to claim 1, comprising a step in which the dehydrogenase is reacted in the presence of at least one substance selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid and citric acid.

[Item 3] The method according to claim 1, comprising a step in which the dehydrogenase is reacted in the presence of one or more substances selected from the group consisting of succinic acid, adipic acid, suberic acid, pimeric acid, potassium chloride, ammonium chloride, diammonium hydrogen citrate, malonic acid, L-lysine, taurine, 3,3-dimethylglutaric acid, malic acid, glutaric acid, calcium glycerate, amino-n-butyric acid, sodium glycolate, sodium α-ketoglutarate, fumaric acid, glycine, glutamic acid and serine.

[Item 4] The method for lowering a reactivity on maltose in the measurement of glucose according to claim 1, wherein the total added amount of one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid is 0.05% by weight or more (as the percent by weight in solution).

[Item 5] The method according to claim 1, wherein the pH during measurement is 7.0 or lower.

[Item 6] The method according to claim 1, wherein the pH is 6.0 or lower.

[Item 7] The method according to claim 1, wherein the reaction is carried out in the presence of at least one mediator.

[Item 8] The method according to claim 7, wherein the mediator is a ferricyanide salt.

[Item 9] The method according to claim 1, wherein the modified pyrroloquinoline quinone dependent glucose dehydrogenase subjected to amino acid sequence modification is a pyrroloquinoline quinone dependent glucose dehydrogenase having a lowered reactivity on maltose as compared with the corresponding wild-type enzyme.

[Item 10] The method for lowering a reactivity on maltose in glucose measurement comprising a step of reacting an modified pyrroloquinoline quinone dependent glucose dehydrogenase according to claim 1, wherein the step of reacting the modified pyrroloquinoline quinone dependent glucose dehydrogenase is carried out in a reagent composition for measuring glucose that contains an modified pyrroloquinoline quinone dependent glucose dehydrogenase subjected to amino acid modification.

[Item 11] The method according to claim 10, wherein the composition for measuring glucose adopts a form in which the composition is contained in a glucose assay kit.

[Item 12] The method according to claim 10, wherein the step of reacting the modified pyrroloquinoline quinone dependent glucose dehydrogenase is carried out in a glucose sensor containing an modified pyrroloquinoline quinone dependent glucose dehydrogenase subjected to amino acid sequence modification and electrodes at least comprising a working electrode and a counter electrode.

[Item 13] The method according to claim 12, wherein the reaction in the glucose sensor comprises applying a voltage to a reaction solution containing the modified pyrroloquinoline quinone dependent glucose dehydrogenase, and measuring the oxidation current of a mediator.

[Item 14] A composition for measuring glucose comprising an modified pyrroloquinoline quinone dependent glucose dehydrogenase subjected to amino acid sequence modification, and one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid, wherein a reactivity on maltose is lowered.

[Item 15] A glucose sensor comprising a modified pyrroloquinoline quinone dependent glucose dehydrogenase subjected to amino acid sequence modification, and one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid, wherein a reactivity on maltose is lowered.

[Item 16] A method for producing a composition for measuring glucose having a lowered reactivity on maltose in which an modified pyrroloquinoline quinone dependent glucose dehydrogenase is used, the method comprising a step of containing one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

[Item 17] A method for producing a glucose sensor having a lowered reactivity on maltose, in which an modified pyrroloquinoline quinone dependent glucose dehydrogenase is used, the method comprising a step containing one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

The composition and measurement method of the present invention is useful for measuring glucose in clinical tests, food analyses and so on. The present invention allows analyses of higher precision by applying to a glucose assay kit or glucose sensor that uses PQQGDH.

The following provides a detailed explanation of the present invention.

One embodiment of the present invention is a method for lowering activity with respect to maltose in glucose measurement that contains a step that reacts an modified pyrroloquinoline quinone dependent glucose dehydrogenase subjected to amino acid sequence modification, wherein a step is contained in which said enzyme is reacted in the presence of one or more substances selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

The PQQGDH used in the present invention is an modified PQQGDH in which the amino acid sequence of wild type of PQQDGH has been modified. Modification of the amino acid sequence here refers to substitution, insertion or deletion of at least one amino acid residue in the original amino acid sequence by genetic engineering techniques. In particular, it is preferable to use an modified PQQGDH in which activity with respect to maltose has been lowered in comparison with the corresponding wild type enzyme as a result of subjecting to such amino acid sequence modification.

The activity with respect to maltose in glucose measurement can be further lowered by reacting the modified PQQGDH in the presence of at least one substance selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

In the present invention, activity for maltose means the action of PQQGDH dehydrogenating that sugar substrate.

In addition to maltose, activity for at least one other sugar other than glucose selected from the sugars other than maltose can also be lowered.

Sugar substrates other than glucose selected from the sugars other than maltose include for example galactose, mannose, xylose and other simple sugars, sucrose, lactose, cellobiose and other disaccharides, maltotriose, maltotetraose and other oligosaccharides, icodextrin (glucose polymer) and other polysaccharides (an oligosaccharide comprises 2 to 10 molecules of a single sugar while a polysaccharide comprises 11 or more molecules of a single sugar bound together by glycoside bonds or the like, with no restrictions on the binding mode, and in the case of a disaccharide or higher sugar the structure may be homogenous or heterogeneous), as well as the sugar alcohols, 2-deoxy-D-glucose, 3-o-methyl-D-glucose and the like and derivatives of these.

Of these, it is preferably to select various sugars which may pose a problem when the modified PQQGDH of the present invention is used for clinical diagnosis or controlling the blood glucose levels of diabetes patients, or for measuring blood glucose concentrations. Examples of such sugars include mannose, allose, xylose, galactose, maltose and the like, and more desirable examples are galactose and lactose. Maltose is the most desirable example.

Furthermore, in the specification of the present application, reduction of activity with respect to maltose or a sugar substrate selected from at least one sugar substrate other than maltose as compared with the corresponding wild type PQQGDH also represents improvement of substrate specificity.

The following method is used to judge whether activity for a specific sugar has been lowered.

In the activity measurement method described in Test Example 1 and Example 7 below, using PQQGDH, the PQQGDH activity value (a) using D-glucose as the substrate solution and the PQQGDH activity value (b) using this sugar in place of D-glucose as the substrate solution are measured, and the relative value ($(b)/(a)\times100$) is calculated given 100 as the measurement value using glucose as the substrate. The same operation is then repeated with the conditions changed, and the values are compared and evaluated.

Activity is measured by the activity measurement method described in Test Example 1 and Example 7 below.

The PQQGDH that can be used in the method of the present invention is an enzyme (EC 1.1.5.2 (old EC 1.1.99.17)) having pyrroloquinoline quinone as the coenzyme which catalyzes a reaction in which D-glucose is oxidized to produce D-glucono-1,5-lactone, with no particular limits on its derivation or structure.

PQQGDH can be classified into a soluble form and a membrane-bound form. Among these, that which originates in *Acinetobacter* is known as soluble PQQGDH, while that present in other microorganisms such as *Escherichia coli* is known as membrane-bound PQQGDH.

The modified PQQGDH of the present invention can be prepared for example by obtaining a gene coding for wild-type PQQGDH, and modifying it to construct a polynucleotide coding for modified PQQGDH, and then using that polynucleotide to produce expression in a suitable expression system.

An origin of a wild type PQQGDH to prepare a modified PQQGDH for use in the invention is not specifically limited. Representative origins of the wild type PQQGDH which is the source of the modification are microorganisms exemplified below. Specifically, examples may include oxidizing bacteria such as *Acinetobacter baumannii* (JP HEI-11-243949 A), *Acinetobacter calcoaceticus* (eg. A. M. Cleton-Jansen et al J. Bacteriol., 170, 2121 (1988); and Mol. Gen. Genet., 217, 430 (1989)), *Pseudomonas aeruginosa, Pseudomonas putida, Pseudomonas fluorescens* and *Gluconobacter oxydans*, and enterobacteria such as *Agrobacterium radiobacter, Escherichia coli* (A. M. Cleton-Jansen et al J. Bacteriol., 172, 6308(1990)) and *Klebsiella aerogenes, Burkhorderia cepacia.*

It is preferable to select those derived from the microorganisms belonging to the genus *Acinetobacter* as the origin. These are water-soluble enzymes and easily dissolved in an aqueous system. More preferably, it is preferable to select the soluble PQQGDH from *Acinetobacter calcoaceticus* or *Acinetobacter baumannii*. Particularly preferable PQQGDHs are derived from *Acinetobacter baumannii* NCIMB 11517 strain (see, JP HEI-11-243949 A), *Acinetobacter calcoaceticus* LMD79.41 strain (see, A. M. Cleton-Jansen et al J. Bacteriol., 170, 2121 (1988); and Mol. Gen. Genet., 217, 430 (1989)), and *Acinetobacter calcoaceticus* IFO 12552 strain (see, JP 2004-173538 A). Most preferable are PQQGDH derived from *Acinetobacter baumannii* NCIMB 11517 strain. The *Acinetobacter baumannii* NCIMB11517 strain was previously classified into *Acinetobacter calcoaceticus.*

In all of these cases, the amino acid sequences and gene sequences are known, or purification methods have been established and the physiochemical properties of the enzyme are known, so that a person skilled in the art can easily prepare modified PQQGDH based on these findings.

The enzyme used in the method of the present invention is an modified pyrroloquinoline quinone dependent glucose dehydrogenase subjected to alteration of the amino acid sequence, and is an modified pyrroloquinoline quinone dependent glucose dehydrogenase having lowered activity with respect to maltose as compared with the corresponding wild type enzyme.

Such modification can easily be performed by the skilled artisan according to known techniques in the art. A variety of methods for introducing a site-directed mutagenesis to a protein by substituting or inserting one or more bases to a nucleotide sequence of a gene coding for the protein are disclosed in Sambrook et al, Molecular Cloning; A Laboratory Manual $2^{nd}$ Edition (1989) Cold Spring Harbor Laboratory Press, New York.

Preferable examples of the modified PQQGDH used in the present invention include PQQGDH that has been subjected to modification of the amino acid sequence at one or more locations in the vicinity of the activity center, and may be subjected to other modifications of the amino acid sequence in addition to that in the vicinity of the activity center. Specific examples include PQQGDH subjected to modification targeted at at least one location selected from the group comprising Pro at position 67, Glu at position 68, Ile at position 69, Gln at position 76, Lys at position 89, Glu at position 129, Lys at position 130, Pro at position 131, Asn at position 167, Gln at position 168, Leu at position 169, Ala at position 170, Tyr at position 171, Leu at position 174, Asn at position 188, Ser at position 189, Ser at position 207, Phe at position 215, Thr at position 224, Ala at position 236, Glu at position 245, Asn at position 249, Lys at position 300, Glu at position 341, Met at position 342, Ala at position 343, Thr at position 349 and Ala at position 351, or at least one location among the same locations described above in pyrroloquinoline quinone dependent glucose dehydrogenase originating in other *Acinetobacter* species or other genii. Furthermore, the amino acid sequence of wild type PQQGDH originating in *Acinetobacter baumannii* strain NCIMB11517 is shown in SEQ. ID NO. 1. In the case the modified PQQGDH has modified amino acid residues at two or more locations, examples of the modified PQQGDH include modified PQQGDH containing one or more modifications targeted at least one of the locations selected from the above-mentioned group.

Furthermore, the amino acid sequence of wild type PQQGDH originating in *Acinetobacter baumannii* strain NCIMB11517 is shown in SEQ. ID NO. 1. In SEQ. ID NO. 1, the amino acids are numbered by designating aspartic acid as 1 after excluding the signal sequence.

Comparisons of the amino acid sequence of PQQGDH originating in *Acinetobacter baumannii* strain NCIMB 11517 (the amino acid sequence of which is indicated in SEQ. ID NO. 1, while the gene sequence is indicated with SEQ. ID NO. 2) with the amino acid sequence of PQQGDH originating in *Acinetobacter calcoaceticus* strain LMD79.41 and the amino acid sequence of PQQGDH originating in *Acinetobacter calcoaceticus* strain IFO 12552 reveal that there are differences only at a small number of locations, and that they are extremely similar with homologies of 92.3% and 91.3%, respectively (including the signal sequence in both cases) (FIGS. 1 and 2).

Thus, a person with ordinary skill in the art would be able to easily recognize that a certain residue in SEQ. ID NO. 1 corresponds to which amino acid residue (at the same location) of PQQGDH originating in *Acinetobacter calcoaceticus* strain LMD79.41. Moreover, an modified PQQGDH having lowered activity with respect to at least one sugar substrate selected from sugar substrates other than glucose as compared with the corresponding wild type PQQGDH can be obtained by carrying out an amino acid mutation at one or more of such locations.

Furthermore, the modified PQQGDH of the present invention may contain a deletion, substitution or insertion and so on at another portion of the amino acid sequence, or other amino acid residues may be added or substituted, provided the activity with respect to glucose is essentially maintained and preferably, there is substantially no detrimental effect on activity with respect to maltose.

Moreover, the modified PQQGDH of the present invention may include an aspect thereof in which a tag such as a histidine tag is bound or inserted into the PQQGDH provided activity with respect to glucose is substantially maintained, and preferably, activity with respect to maltose is not substantially adversely affected, an aspect thereof in which another peptide or another protein (such as streptoavidin or cytochrome) is fused to at least one end of PQQGDH, an aspect thereof in which PQQGDH is chemically modified by a sugar chain or other compound, and an aspect thereof such as that which has been cross-linked by a disulfide bond and so forth within and/or between PQQGDH molecules or that which has been linked via a linker peptide and so forth. Alternatively, the modified PQQGDH may also include that which has been composed by combining fragments of wild type PQQGDH from several sources.

GLD-321 produced by Toyo Boseki K.K. and other commercial products can be used for these PQQGDH enzymes. Alternatively, they can be easily manufactured by a person skilled in the art using known techniques in the field.

For example, naturally-occurring microorganisms producing the PQQGDH, or transformant prepared by inserting a naturally-occurring or modified PQQGDH gene into an expression vector (a variety of vectors including a plasmid are known), followed by transforming a suitable host (a variety of hosts including *E. coli* are known) with the expression vector, are cultured, host cells are collected from a culture medium by centrifugation, cells are broken down mechanically or enzymatically with lysozyme, optionally solubilized by the addition of a chelating agent such as EDTA or a surfactant to obtain a water soluble fraction containing PQQGDH. The expressed PQQGDH can be secreted to a culture medium using a suitable host-vector system.

PQQGDH can be separated and precipitated from the PQQGDH-containing solution by concentration under reduced pressure, membrane concentration, salting out using ammonium sulfate or sodium sulfate, or a fractional precipitation with a hydrophilic solvent such as methanol, ethanol, acetone, etc. Heat treatment and isoelectric treatment are also an effective purification method. Purified PQQGDH can be obtained by gel filtration with adsorbent or gel filtering agent, adsorption chromatography or affinity chromatography. The standard enzyme is preferably purified enough to show a single band in electrophoresis (SDS-PAGE).

These can be carried out according to, for example, the documents indicated below.

(a) Protein Experimental Protocols, Vol. 1, Protein Analysis Edition, Vol. 2, Structural Analysis Edition (Shujunsha Publishing), Yoshifumi Nishimura, Yoshio Ohno, editors
(b) Revised Protein Experimental Notes, Part 1, Extraction, Separation and Purification (Yodosha Publishing), Masato Okada, Kaoru Miyazaki, editors
(c) Procedures for Protein Experimentation (Yodosha Publishing), Masato Okada, Kaoru Miyazaki, editors The PQQGDH can be heat-treated at 25 to 50° C., preferable 30 to 45° C. to increase a proportion of holoenzyme to the total GDH protein before or after the above-mentioned steps.

Concentration of PQQGDH of the invention is not specifically limited.

In an embodiment of the invention, enzymatic activity of PQQGDH can be measured according to the following method.

Method for Assaying Enzymatic Activity of PQQGDH (1) Principle of Measurement

D-glucose+PMS+PQQGDH→D-glucono-1,5-lactone+PMS (red) 2PMS (red)+NTB→2PMS+diformazan The presence of diformazan formed by reduction of nitrotetrazolium blue (NTB) by phenazine methosulfate (PMS) (red) was measured by spectrophotometry at 570 nm.

(2) Definition of Unit

One unit refers to the amount of the enzyme of PQQGDH to form 0.5 mM of diformazan per one minute under the following condition.

(3) Method

Reagent

A. D-Glucose solution: 1.0 M (1.8 g D-glucose, molecular weight: 180.16)/10 mL $H_2O$
B. PIPES-NaOH buffer pH 6.5: 50 mM (1.51 g of PIPES [molecular weight: 302.36] was suspended in 60 mL of water) was dissolved in 5 N NaOH, and 2.2 mL of 10%

Triton X-100 is added. pH was adjusted to 6.5±0.05 at 25 (C using 5 N NaOH, and water was added to make 100 mL.)

C. PMS solution: 3.0 mM (9.19 mg of phenazine methosulfate [molecular weight: 817.65])/10 mL $H_2O$ D. NTB solution: 6.6 mM (53.96 mg of nitrotetrazolium blue [molecular weight: 817.65])/10 mL $H_2O$ E. Enzyme dilution solution: 50 mM PIPES-NaOH buffer (pH 6.5) containing 1 mM $CaCl_2$, 0.1% Triton X-100 and 0.1% BSA Procedure The following reaction mixture was prepared in a light shielding bottle, and stored on ice (prepared at use).

1. 0.9 mL of D-glucose solution (A)
   25.5 mL of PIPES-NaOH solution (pH 6.5) (B)
   2.0 mL of PMS solution (C)
   1.0 mL of NTB solution (D)

| Concentration in assay mixture | |
|---|---|
| PIPES buffer | 42 mM |
| D-glucose | 30 mM |
| PMS | 0.20 mM |
| NTB | 0.22 mM |

2. The reaction mixture (3.0 mL) was placed in a test tube (made from plastic), which was then preliminarily heated at 37° C. for 5 minutes.
3. The enzyme solution (0.1 mL) was added, and mixed by gently inverting.
4. The increase of absorbance for water at 570 nm was recorded by a spectrophotometer for 4 to 5 minutes with keeping the temperature at 37° C., and ΔOD per minute was calculated from an initial linear part of a curve (OD test).

At the same time, the same method except for adding the enzyme dilution solution (E) in place of the enzyme solution was repeated to measure a blank (ΔOD blank).

The enzyme powder was dissolved in the ice-cooled enzyme dilution solution (E) just before the assay, and diluted with the same buffer to 0.1 to 0.8 U/mL (due to adhesiveness of the enzyme, it is preferable to use the plastic tube).

Calculation

The activity is calculated using the following formulae:

$$U/ml=\{\Delta OD/min(\Delta OD\ test-\Delta OD\ blank)\times Vt\times df\}/(20.1\times 1.0\times Vs)$$

$$U/mg=(U/ml)\times 1/C$$

Vt: total volume (3.1 mL)

Vs: sample volume (1.0 mL)

20.1: ½ mM molecular absorbance coefficient of diformazan 1.0: light path length (cm)

df: dilution factor

C: enzyme concentration in solution (c mg/mL)

Commercially available reagents can be used for any of the one or more substances selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid used in the method of the present invention.

The total added amount of one or more substances selected from the above-mentioned group is preferably 0.05% (as percent by weight in solution) or more. Furthermore, the “solution” referred to here includes a solution in the step in which glucose dehydrogenase is dissolved in solution when producing a glucose sensor.

Examples of forms in which substances are supplied include liquids and solids. Among these, a dry powder is preferable. In addition, the buffer content (w/w) in a powder composition is preferably 0.1 to 10%, more preferably 0.2 to 5%, and even more preferably 0.2 to 2%.

The method of the present invention may also be comprised such that the step that reacts the modified pyrroloquinoline quinone dependent glucose dehydrogenase is carried out in a reagent composition for measuring glucose that contains modified pyrroloquinoline quinone dependent glucose dehydrogenase subjected to amino acid sequence modification.

Moreover, the composition for measuring glucose may be in a form that is contained in a glucose assay kit.

The method of the present invention may also be comprised such that the step of reacting modified pyrroloquinoline quinone dependent glucose dehydrogenase is carried out in a glucose sensor that contains modified pyrroloquinoline quinone dependent glucose dehydrogenase subjected to amino acid sequence modification and electrodes at least composed of a working electrode and a counter electrode.

Moreover, the method of the present invention may also be comprised of a step that reacts modified pyrroloquinoline quinone dependent glucose dehydrogenase, wherein the reaction in the glucose sensor is comprised of applying a voltage to a reaction solution containing modified pyrroloquinoline quinone dependent glucose dehydrogenase, and measuring the oxidation current of a mediator.

Moreover, the present invention is a composition for measuring glucose having lowered activity with respect to maltose in a composition for measuring glucose using modified pyrroloquinoline quinone dependent glucose dehydrogenase, or a glucose sensor having lowered activity with respect to a maltose in a glucose sensor using modified pyrroloquinoline quinone dependent glucose dehydrogenase, comprising modified pyrroloquinoline quinone dependent glucose dehydrogenase subjected to amino acid sequence modification and one or more substances selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

The composition may adopt various forms, including a liquid or other aqueous composition (i.e., aqueous solution or suspension), a powder obtained by vacuum drying or spray drying, or a form obtained by freeze-drying, and there are no particular limitations thereon. There are no particular limitations on the freeze-drying method, and freeze-drying may be carried out in accordance with ordinary methods. A composition containing the enzyme of the present invention is not limited to a freeze-dried product, and may also be in a liquid state reconstituted from a freeze-dried product.

In the case a composition containing the enzyme of the present invention composes a portion of a glucose sensor as well, the composition may similarly adopt various forms, including a liquid or other aqueous composition (i.e., aqueous solution or suspension), a powder obtained by vacuum drying or spray drying, or a form obtained by freeze-drying, and there are no particular limitations thereon. There are no particular limitations on the freeze-drying method, and freeze-drying may be carried out in accordance with ordinary methods. A composition containing the enzyme of the present invention is not limited to a freeze-dried product, and may also be in a liquid state reconstituted from a freeze-dried product.

Moreover, the present invention is a production method of a composition for measuring glucose having lowered activity with respect to maltose in a composition for measuring glucose using modified pyrroloquinoline quinone dependent glucose dehydrogenase, or a production method of a glucose sensor having lowered activity with respect to a maltose in a glucose sensor using modified pyrroloquinoline quinone dependent glucose dehydrogenase, comprising a step that contains one or more substances selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium $\alpha$-ketoglutarate, fumaric acid, glycine, glutamic acid, serine and citric acid.

In the method of the present invention, various buffers can be used during measurement. A typically used buffer may be used for the buffer, and normally that which adjusts the pH of the composition to 5 to 10 is preferable. Examples of buffers include tris-hydrochloric acid, boric acid, phosphoric acid, acetic acid, citric acid, succinic acid, phthalic acid, glutaric acid, maleic acid, glycine and salts thereof, as well as Good's buffers such as MES, Bis-Tris, ADA, PIPES, ACES, MOPSO, BES, MOPS, TES and HEPES.

However, buffers that do not form an insoluble salt with calcium are preferable. A buffer such as a phosphoric acid buffer that forms an insoluble salt with calcium is not preferable. In addition, buffers having a terminal amino group such as tris-aminomethane are not preferable since they destabilize the PQQ bond of PQQ dependent glucose dehydrogenase.

Consequently, more preferable examples of buffers include buffers such as boric acid and acetic acid as well as Good's buffers such as BES, Bicine, Bis-Tris, CHES, EPPS, HEPES, HEPPSO, MES, MOPS, MOPSO, PIPES, POPSO, TAPS, TAPSO, TES and Tricine. Among these, those such as PIPES having the ability to buffer to a pH of 6 to 7 are preferable. In addition, the content (w/w) of buffer in a powder composition is preferably 1.0 to 50% and more preferably 5 to 10%.

Buffers can be used alone or in combination of two or more. Composite buffers containing one or more buffers other than above-mentioned buffers can also be used.

A concentration of added buffer is not specifically limited, as long as it is within a concentration range with sufficient buffer capacity, but preferably 100 mM or less, more preferably 50 mM or less, and also 5 mM or more.

A buffer content in a lyophilized product is not specifically limited, but preferably 0.1 mass %, particularly preferably 0.1 to 30 mass %.

A variety of buffers are commercially available.

The buffer can be added to a reaction mixture when use, or preliminarily included when a glucose assay reagent, a glucose assay kit, or a glucose sensor described later is prepared. The buffer is added in any form such as liquid or dry powder, as long as it acts in measurement conditions.

Improving substrate specificity in the present invention means improving reactivity of the PQQGDH enzyme for glucose or for a sugar other than glucose. Examples of sugars other than glucose include particularly the disaccharides maltose, sucrose, lactose, cellobiose and the like, especially maltose. In the invention of this application, a decrease in activity for a disaccharide is also described as an improvement in substrate specificity.

The following method is used to evaluate whether activity for a disaccharide has been lowered.

In the activity measurement method described in Test Example 1 below, using PQQGDH, the PQQGDH activity value (a) using D-glucose as the substrate solution and the PQQGDH activity value (b) using this disaccharide in place of D-glucose as the substrate solution are measured, and the relative value ($(b)/(a)\times 100$) is calculated given 100 as the measurement value using glucose as the substrate.

In addition, the present invention includes method for lowering activity with respect to maltose in glucose measurement comprising a step that reacts modified pyrroloquinoline quinone dependent glucose dehydrogenase containing a mediator that contributes to electron transfer in the form of a composition. There are no particular limitations on the mediator described in the present patent, and examples include phenazine methosulfate (PMS), 2,6-dichlorophenol-indophenol (DCPIP), ferrocene and derivatives thereof, and ferricyanides. Moreover, examples also include methoxyphenazine methosulfate (PMS), combinations of phenazine methosulfate (PMS) and 2,6-dichlorophenol-indophenol (DCPIP), combinations of PMS and nitro blue tetrazolium (NBT), DCPIP alone and ferrocene alone. Ferricyanide salts are used more preferably, while potassium ferricyanide is used most preferably.

A concentration of an added mediator is unnecessary to determined in a specific range due to variation of sensitivity of mediators, but is generally at least 1 mM.

The mediator can be added to a reaction mixture when use, or preliminarily included when a glucose assay reagent, a glucose assay kit, or a glucose sensor described later is prepared. The mediator is added in any form such as liquid or dry powder, as long as it acts in measurement conditions.

A variety of components including surfactants, stabilizers, carriers and excipients can be added to the assay system of the invention For example, PQQGDH can be stabilized still further by addition of calcium ions or salts thereof and glutamic acid, glutamine, lysine and other amino acids as well as serum albumin and the like.

For example, PQQGDH can be stabilized by the addition of calcium ion or one or more calcium salts. Calcium salts include calcium salts with inorganic acids or organic acids such as calcium chloride, calcium acetate and calcium citrate. Calcium ion content in an aqueous composition is preferably $1\times10^{-4}$ to $1\times10^{-2}$ M.

The stabilizing effect based on the addition of calcium ion or calcium salt or salts is further improved by the addition of one or more amino acids selected from the group consisting of glutamic acid, glutamine and lysine. Bovine serum albumin (BSA) and/or ovalbumin can also be included. In addition, PQQGDH can be stabilized by a combination of (i) one or more compounds selected from the group consisting of aspartic acid, glutamic acid, $\alpha$-ketoglutaric acid, malic acid, $\alpha$-ketogluconic acid and $\alpha$-cyclodextrin, and (ii) albumin.

One aspect of the present invention is a method for measuring glucose comprising a step that reacts modified PQQGDH subjected to amino acid sequence modification that reduces activity with respect to maltose in glucose measurement comprising, a step that reacts modified PQQGDH containing a step in which the modified PQQGDH is reacted in the presence of at least one type of substance having two or more carboxyl groups per molecule thereof.

In the method of the present invention that reduces activity with respect to maltose in glucose measurement comprising a step that reacts modified PQQGDH, the substance that is present with the PQQGDH is at least one type of substance selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid. These substances have the common characteristic of having two or more carboxyl groups per molecule, and may or may not have a different functional group such as hydrosyl group or keto group in a molecule thereof. Alternatively, these substances may also be characterized as dicarboxylic acids or tricarboxylic acids.

A method for lowering activity with respect to maltose in glucose measurement comprising a step that reacts modified pyrroloquinoline quinone dependent glucose dehydrogenase may also contain a buffer component, surfactant, metal salt to maximally demonstrate the activity and stability of PQQGDH, hydrophilic polymer and various types of stabilizers and so on. There are no particular limitations on the buffer component, and examples include Good's buffers such as potassium phosphate, sodium phosphate, PIPES and MES, as well as acetic acid, glycine and boric acid. In addition, there are no particular limitations on the surfactant, and examples include various types of Triton, Tween, bile acids and SDS. In addition, compounds containing calcium, which are known to bind to the active center, are preferable examples of metal salts. Examples of stabilizers include proteins such as bovine serum albumin and ovalbumin, and amino acids represented by glutamine, lysine and glutamic acid.

There are no particular limitations on the content of the substance having two or more carboxyl groups in a molecule thereof contained in the method of the present invention that reduces activity with respect to maltose in glucose measurement comprising a step that reacts modified pyrroloquinoline quinone dependent glucose dehydrogenase provided it is within a range that is effective in improving substrate specificity, and is preferably 0.4% or more and more preferably 2 to 80% in the case said composition is a solid in the manner of a freeze-dried product. In addition, the concentration of the substance having two or more carboxyl groups in a molecular thereof is preferably 1 mM or more and more preferably 5 to 100 mM in the case said composition is a liquid.

In addition, from a different viewpoint, the preferable content of the substance having two or more carboxyl groups in a molecule thereof in said solid or liquid composition is preferably 10 molecules or more per molecule of PQQGDH present, and more preferably 103 to 107 molecules per molecule of PQQGDH present.

In addition, the method of the present invention that reduces activity with respect to maltose in glucose measurement comprising a step that reacts modified pyrroloquinoline quinone dependent glucose dehydrogenase is thought to demonstrate the effect thereof if it is within a pH range that is less than the isoelectric point of said PQQGDH and which causes the charge on the surface of the PQQGDH to be positive, and the upper limit of that range is roughly pH 9.0. However, the pH during the measurement reaction is preferably 7.0 or lower and more preferably 6.0 or lower to lower the absolute value of maltose activity. The lower limit is not particularly limited provided the PQQGDH demonstrates activity, and is preferably 4.0 or higher and more preferably 5.0 or higher.

Adjustment of pH may be carried out in advance during production of the composition, or it may be carried out immediately prior to measurement. Adjustment of pH may be carried out in accordance with ordinary methods, such as by suitably adding an acid such as hydrochloric acid, phosphoric acid or acetic acid or a base such as KOH or NaOH while monitoring pH.

In the method of the present invention that reduces activity with respect to maltose in glucose measurement comprising a step that reacts modified pyrroloquinoline quinone dependent glucose dehydrogenase, the carboxyl group of the added carboxylic acid is thought to have charge affinity with a residue having a positive charge of the portion of the PQQGDH that contacts a solvent, namely a residue such as lysine or arginine. This is because the addition of two or more carboxyl groups per molecule of substance requires a carboxyl group that is adsorbed due to the charge affinity with the surface of PQQGDH as well as one or more free carboxyl groups. In the case the reactivity to disaccharides of the modified PQQGDH used in the present invention decreases, a change occurs in the mode of interaction between the reaction center and substrate due to modification of the amino acid sequence. If maltose is used as an example of a disaccharide, although it is thought that the hydroxyl group at position 1 of one of the rings of maltose is oxidized to form a ketone in the reaction with PQQGDH, in the case of modified PQQGDH in which substrate specificity has changed, it does not contribute to the reaction, namely there is greater susceptibility to the effect of physicochemical interaction on the side of the ring that is not recognized as the active center, and this is thought to lead to the result of a change in substrate specificity. In this type of situation, it can be surmised that the free carboxyl group possessed by carboxylic acid adsorbed to the surface of PQQGDH contributes to impairment of the affinity of maltose with the active center site. Those sites on PQQGDH where carboxylic acid molecules directly contributing to this effect are adsorbed are thought to be lysine residues at positions 28, 142, 292 and 300 or an arginine residue at position 45. The free carboxyl group of carboxylic acid charge-bonded to this site is surmised to lead to action that impairs the affinity of disaccharides to the active center. In addition, although the pH at the time of measurement in the present invention is preferably 7.0 or lower and more preferably 6.0 or lower, this is thought to be because this enables the above-mentioned interaction to be demonstrated more effectively in the state in which the positive charge of the portion of said PQQGDH that contacts solvent is stronger.

On the basis of this theory, modified PQQGDH for which improvement of substrate specificity is observed as compared with the wild type in terms of its original characteristics is predicted to be effective, regardless of the degree, in further improving substrate specificity during glucose measurement reactions by carrying out the present invention.

Another aspect of the present invention comprises a method for lowering activity with respect to maltose in glucose measurement comprising a step that reacts modified PQQGDH wherein the step that reacts modified PQQGDH is carried out in a reagent composition for measuring glucose that contains modified PQQGDH subjected to amino acid sequence modification.

At this time, the present invention may also be still another aspect in which the composition for glucose measurement is contained in a glucose assay kit. In addition, the compound having a carboxyl group may be added immediately before adding the measurement target in the form of a glucose-containing specimen, or it may be added in advance during production of the composition. In addition, in the method of the present invention, various types of buffer components, metal salts, surfactants, hydrophilic polymers and various types of stabilizers and so on may be contained in the composition in advance or may be added at the time of measurement. Examples of these components are as previously described.

Another aspect of the present invention comprises a method for lowering activity with respect to maltose in glucose measurement comprising a step that reacts modified PQQGDH wherein the step that reacts the modified PQQGDH is carried out in a glucose sensor containing modified PQQGDH subjected to amino acid sequence modification and at least electrodes comprising a working electrode and a counter electrode.

At this time, the present invention may also be still another aspect in which the reaction in the glucose sensor is comprised of applying a voltage to a reaction solution containing modified PQQGDH and measuring the oxidation current of a mediator. Alternatively, the present invention may also include a reference electrode. In addition, the glucose sensor may be in a form in which the PQQGDH and mediator are sealed in a device while preventing from flowing out, or a form that allows continuous measurement immobilized on a substrate. In addition, the present invention may also be in a form in which the PQQGDH and mediator are interchangeably provided on a chip.

Still another aspect of the present invention comprises a composition for glucose measurement or a glucose sensor having lowered activity with respect to maltose in composition for measuring glucose using modified PQQGDH that contains modified PQQGDH subjected to amino acid sequence modification and a substance having two or more carboxyl groups per molecule thereof selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

Still another aspect of the present invention comprises a method for producing a composition for measuring glucose or a glucose sensor having lowered activity with respect to maltose in a composition for measuring glucose using modified pyrroloquinoline quinone dependent glucose dehydrogenase comprising a step that contains a substance having two or more carboxyl groups per molecule thereof selected from the group comprising succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

In each of the above-mentioned aspects, the modified PQQGDH, composition for measuring glucose, glucose assay kit and glucose sensor of the present invention may be in various forms such as a liquid (e.g., aqueous solution, suspension), powder or freeze-dried product. There are no particular limitations on the freeze-drying method, and freeze-drying may be carried out in accordance with ordinary methods. A composition containing the enzyme of the present invention is not limited to a freeze-dried product, and may also be in a liquid state reconstituted from a freeze-dried product.

Although varying according to the enzyme source, the content of PQQGDH in a freeze-dried composition is preferably within the range of about 5 to 50% (weight ratio). When converted to enzyme activity, the content is preferably within the range of 100 to 2000 U/mg.

Moreover, in each of the above-mentioned aspects, the modified PQQGDH, composition for glucose measurement, glucose assay kit and glucose sensor of the present invention may be in a purified state according to the form and method of use. Other components such as surfactants, stabilizers, vehicles and various other additives may be added as necessary.

There are no particular limitations on the method used to incorporate these additives in the present invention, and examples of methods used include incorporating a stabilizer in a buffer containing PQQGDH, a method in which PQQGDH is incorporated in a buffer containing a stabilizer, and a method in which PQQGDH and stabilizer are incorporated in a buffer simultaneously.

For example, modified PQQGDH can be further stabilized by having (1) one type or two or more types of compounds selected from the group comprisingting aspartic acid, glutamic acid, α-ketoglutaric acid, malic acid, α-ketogluconic acid and α-cyclodextrin and salts thereof, and (2) albumin present with the modified PQQGDH.

There are no particular limitations on the salts of consisting aspartic acid, glutamic acid, α-ketoglutaric acid, malic acid and α-ketogluconic acid, and examples of salts include sodium, potassium, ammonium, calcium and magnesium salts. The amount of the above-mentioned compounds, salts thereof and α-cyclodextrin added is preferably within the range of 1 to 90% (weight ratio). These substances may be used alone or as a combination of a plurality of types thereof.

In addition, stabilization effects are also obtained by adding calcium ion. Namely, modified protein can be stabilized by adding calcium ion or calcium salt. Examples of calcium salts include calcium salts of inorganic acids or organic acids such as calcium chloride, calcium acetate or calcium citrate. In addition, the content of calcium ion in an aqueous composition is preferably $1\times10^{-4}$ to $1\times10^{-2}$ M.

Stabilization effects resulting from containing calcium ion or calcium salt are further improved by containing an amino acid selected from the group consisting of glutamic acid, glutamine and lysine.

An amino acid selected from the group consisting of glutamic acid, glutamine and lysine may be one type or two or more types. In the above-mentioned aqueous composition, the content of amino acid selected from the group consisting of glutamic acid, glutamine and lysine is preferably 0.01 to 0.2% by weight.

In addition, a glycosylureide compound such as N-carbamoyl-β-D-glucopyranosylamine can also be used as a freeze-drying stabilizer.

There are no particular limitations on contained buffers, examples of which include Tris buffers, phosphoric acid buffers, boric acid buffers and Good's buffers, and all buffers that do not form an insoluble salt with calcium can be used. The pH of said buffer is adjusted within the range of about 5.0 to 10.0 according to the purpose of use. There are no particular limitations on the content of buffer in a freeze-dried product, it is preferably used at 0.1% (weight ratio) or more, and particularly preferably 0.1 to 30% (weight ratio).

In addition, serum albumin may also be contained. In the case of adding serum albumin to the above-mentioned aqueous composition, the content thereof is preferably 0.05 to 0.5% by weight.

Examples of albumin that can be used include bovine serum albumin (BSA) and ovalbumin (OVA), with BSA being particularly preferable. The content of said albumin is preferably within the range of 1 to 80% (weight ratio) and more preferably within the range of 5 to 70% (weight ratio).

On the other hand, in each of the above-mentioned aspects, the modified PQQGDH, composition for measuring glucose, glucose assay kit and glucose sensor of the present invention can be composed without containing a protein component other than a protein component originating in the host.

An example of a protein component other than a protein component originating in the host is a bioprotein such as BSA.

As a result of composing in this manner, it is possible to reduce non-specific reactions in a glucose measurement system.

In this case, the composition is basically composed of modified PQQGDH, calcium or calcium salt and buffer.

Examples of forms in which the calcium is supplied include inorganic or organic calcium salts such as calcium chloride, calcium acetate and calcium citrate. In addition, the calcium content (w/w) in a powder composition is preferably 0.05 to 5%.

The buffer may be an ordinarily used buffer, normally that which adjusts the pH of the composition to 5 to 10 is preferable. However, caution must be taken with respect to the addition conditions in the case of phosphoric acid buffers and other buffers having the potential to form an insoluble salt with calcium. In addition, buffers having a terminal amino group in the manner of tris-aminomethane require caution with respect to the addition conditions since they have the potential to destabilize the PQQ bond of PQQ dependent glucose dehydrogenase. Consequently, more preferable examples of buffers include buffers such as boric acid and acetic acid as well as BES, Bicine, Bis-Tris, CHES, EPPS, HEPES, HEPPSO, MES, MOPS, MOPSO, PIPES, POPSO, TAPS, TAPSO, TES and Tricine.

In addition, the buffer content (w/w) in a powder composition is preferably 1.0 to 50%.

In addition, amino acid or organic acid may be further added to a composition basically composed of modified PQQGDH, calcium or calcium salt and buffer.

In addition, the composition may be an aqueous composition or freeze-dried product in the case they are contained.

A glucose level can be determined by a variety of methods of the invention.

The glucose assay reagent, glucose assay kit, or glucose sensor of the invention can be prepared in a variety of forms including liquid (aqueous solution, suspension), powder (prepared by vacuum dry or spray dry), lyophilized form, etc. Lyophilization is not limited and may be carried out according a conventional method. The composition including enzyme of the invention include a lyophilized product and a solution prepared by redissolving the lyophilized product.

A so-called calorimetric method, which uses as an indicator fluctuations in optical absorbance at a specific wavelength attributable to the generation or reduction of color by a mediator or chromogenic reagent, can be adopted for the method for measuring glucose in the present invention, or glucose can be measured based on an oxidation current value of a mediator by applying a voltage to the reaction solution.

In the method for measuring glucose of the present invention, glucose may also be measured by so-called end-point measurement in which a reduced mediator is measured that has accumulated after reacting all of the glucose in a specimen with PQQGDH, or it may be measured by so-called rate measurement in which the enzyme activity of PQQGDH is measured that is dependent on the concentration of the substrate in the form of glucose.

Glucose Measurement Reagent

The glucose measurement reagent of the present invention typically includes PQQGDH, buffers, mediators and other reagents necessary for measurement, a glucose standard solution for preparing the calibration curve, and directions for use. The kit of the present invention can be provided for example as a freeze-dried reagent or as a solution in a suitable storage solution. Preferably the PQQGDH of the present invention is provided in holoenzyme form, but it can also be provided in apoenzyme form and converted to holoenzyme form for use.

Glucose Assay Kit

The glucose assay kit of the present invention typically includes PQQGDH and buffers, mediators and other reagents necessary for measurement, along with a glucose standard solution for preparing the calibration curve and directions for use. The kit of the present invention can be provided for example as a freeze-dried reagent or as a solution in a suitable storage solution. Preferably the PQQGDH of the present invention is provided in holoenzyme form, but it can also be provided in apoenzyme form and converted to holoenzyme form for use.

More specifically, the composition for measuring glucose and the method for measuring glucose of the present invention can adopt the forms indicated below.

Glucose Assay Kit:

The present invention is also a glucose assay kit that contains a composition for measuring glucose according to the present invention. The glucose assay kit of the present invention contains an amount of modified PQQGDH according to the present invention sufficient for at least one assay. Typically, in addition to modified PQQGDH, the kit contains a buffer required for assay, a mediator, glucose standard reagents for preparing a calibration curve and usage instructions. The modified PQQGDH of the present invention can be supplied in various forms such as a freeze-dried reagent or as a solution in a suitable storage solution.

Glucose Sensor:

The present invention is also a glucose sensor that uses a composition for measuring glucose according to the present invention. A carbon electrode, gold electrode or platinum electrode and so on is used for the electrode, and the enzyme of the present invention is immobilized thereon. Examples of immobilization methods include methods using a crosslinking reagent, methods for sealing in a polymer matrix, methods for coating with a dialysis membrane, photocrosslinking polymers, conductive polymers and oxidation-reduction polymers. Alternatively, the enzyme of the present invention may be adsorbed and immobilized in a polymer together with a mediator or these methods may be used in combination. Although the modified PQQGDH of the present invention is preferably immobilized on an electrode in the form of a holoenzyme, it may also be immobilized in the form of an apoenzyme and the PQQ may be provided as a separate layer or in solution. Typically, after immobilizing the modified PQQGDH of the present invention on a carbon electrode using glutaraldehyde, it is treated with a reagent having an amino group to block the glutaraldehyde.

Glucose concentration can be measured as described below. Buffer liquid is placed in a thermostatic cell, $CaCl_2$ is added together with a mediator and the temperature is kept constant. An electrode having the PQQGDH of the present invention fixed thereon is used as the working electrode, together with a counter electrode (such as a platinum electrode) and a reference electrode (such as an Ag/AgCl electrode). A fixed voltage is applied to the carbon electrode, and once the current has become constant a reagent comprising glucose is added and the increase in current is measured. The glucose concentration in the sample is calculated against a calibration curve using a glucose solution of a standard concentration.

BRIEF DESCRIPTION OF THE DRAWINGS

FIG. 1 is a comparison between the amino acid sequence of PQQGDH originating in *Acinetobacter baumannii* strain NCIMB 11517 (upper sequence) (SEQ ID NO: 3) and the amino acid sequence of PQQGDH originating in *Acinetobacter calcoaceticus* strain LMD 79.41 (lower sequence) (SEQ ID NO: 4). Furthermore, in this figure only, the amino acid sequence of PQQGDH originating in *Acinetobacter baumannii* strain NCIMB 11517 designates the starting methionine that contains the signal sequence as 1. The first aspartic acid of SEQ. ID NO. 1 corresponds to the 26th amino acid in this figure.

FIG. 2 is a comparison between the amino acid sequence of PQQGDH originating in *Acinetobacter baumannii* strain NCIMB 11517 (upper sequence) (SEQ ID NO: 5) and the amino acid sequence of PQQGDH originating in *Acinetobacter calcoaceticus* strain IFO 12552 (lower sequence) (SEQ ID NO: 6).

BEST MODE FOR CARRYING OUT THE INVENTION

Although the following provides a more detailed explanation of the present invention based on its examples, it goes without saying that these examples do not limit the scope of the present patent application.

EXAMPLE 1

Production of a Gene-Recombinant Microorganism Producing Modified PQQ Dependent Glucose Dehydrogenase Expression plasmid pNPG5 of wild type PQQ dependent glucose dehydrogenase was inserted with a structural gene encoding PQQ dependent glucose dehydrogenase originating in *Acinetobacter baumannii* strain NCIMB11517 at the multi-cloning site of vector pBluescript SK(−). Mutagenesis treatment was carried out using the QuickChange™ Site-Directed Mutagenesis Kit (Stratagene) in accordance with the protocol thereof based on a synthetic oligonucleotide of about 40 mer containing this recombinant plasmid pNPG5 and a triplet encoding an amino acid at the mutation insertion site in the center thereof to acquire a recombinant plasmid encoding mutant PQQ dependent glucose dehydrogenase respectively substituted with Ala for Gln at position 168, Pro for Leu at position 169, Met for Ala at position 170, Asp for Glu at position 245, Ile for Met at position 342 and Thr for Ala at position 351 (pNPG5−Q168A+L169P+A170M+E245D+M342I+A351T). 5 μg of this pNPG5−Q168A+L169P+A170M+E245D+M342I+A351T DNA were cleaved with BamHI and XhoI (Toyobo) to isolate the structural gene portion of the mutant PQQ dependent glucose dehydrogenase. The isolated DNA and pTM33 cleaved with BamHI and XhoI (1 μg) were reacted for 16 hours at 16° C. with 1 unit of T4 DNA ligase to link the DNA. The linked DNA was then transformed using *Escherichia coli* DH5α competent cells. The resulting expression plasmid was named pNPG6−Q168A+L169P+A170M+E245D+M342I+A351T. This expression plasmid was transformed in *Pseudomonas putida* TE3493 (Fermentation Research Institute Deposit No. 12298) by electroporation, and the resulting transformant produced modified PQQGDH.

TEST EXAMPLE 1

Method for Measuring GDH Activity

Measurement Principle:

D-glucose+PMS+PQQGDH→D-glucono-1,5-lactone+PMS (red)

PMS (red)+DCPIP→PMS+DCPIP (red)

The presence of DCPIP (red) formed by reduction of 6-chlorophenol-indophenol (DCPIP) by phenazine methosulfate (PMS) (red) was measured by spectrophotometry at 600 nm.

Definition of Units:

1 unit refers to the amount of PQQGDH that forms 1.0 millimole of DCPIP (red) per minute under the conditions described below.

(3) Method

Reagents:

A. D-glucose reagent: 1.0 M (1.8 g D-glucose (molecular weight: 180.16)/10 ml $H_2O$)

B. PIPES-NaOH buffer: pH 6.5, 50 mM (1.51 g of PIPES (molecular weight: 302.36) suspended in 60 ml of water dissolved in 5 N NaOH followed by the addition of 2.2 ml of 10% Triton X-100; adjusted to pH of 6.5±0.5 at 25° C. using 5 N NaOH and brought to a final volume of 100 ml by addition of water)

C. PMS solution: 24 mM (73.52 mg of phenazine methosulfate (molecular weight: 817.65)/10 ml $H_2O$)

D. DCPIP solution: 2.0 mM (6.5 mg of nitrotetrazolium blue (molecular weight: 817.65)/10 ml $H_2O$ E. Enzyme diluent: 50 mM PIPES-NaOH buffer containing 1 mM CaCl2, 0.1% Triton X-100 and 0.1% BSA (pH: 6.5)

Procedure:

The following reaction mixture was prepared in a light-protected bottle and stored on ice (prepared at the time of use).

1. 4.5 ml D-glucose solution (A)

21.9 ml PIPES-NaOH solution (pH6.5) (B)

2.0 ml PMS solution (C)

1.0 ml DCPIP solution (D)

The concentrations in this assay mixture were as follows:

PIPES buffer: 36 mM

D-glucose: 148 mM

PMS: 1.58 mM

NTB: 0.066 mM 3.0 ml of the reaction mixture were placed in a test tube (plastic) and pre-warmed for 5 minutes at 37° C.

0.1 ml of enzyme solution was added followed by inverting gently to mix.

The reduction in the absorbance relative to water at 600 nm was recorded for 4 to 5 minutes with a spectrophotometer while maintaining the temperature of the mixture at 37° C., and the ΔOD per minute was calculated from the initial linear portion of the curve (OD test).

At the same time, the same procedure was repeated with the exception of adding enzyme diluent (E) instead of enzyme solution followed by measurement of the blank (ΔOD blank).

Enzyme powder was dissolved with cold enzyme diluent (E) immediately prior to the assay, and then diluted to 0.05 to 0.10 U/ml with the same buffer (the use of plastic tubes is preferable to ensure adhesion of the enzyme).

Calculations:

Activity was calculated using the following formula.

$$U/ml=\{\Delta OD/min(\Delta OD\ test-\Delta OD\ blank)\times Vt\times df\}/(16.8\times 1.0\times Vs)$$

$$U/mg=(U/ml)\times 1/C$$

Vt=Total volume (3.1 ml)

Vs=Sample volume (0.1 ml)

16.8: Millimolar molecular absorption coefficient of DCPIP under the above-mentioned measurement conditions ($cm^2/\mu M$)

1.0: Path length (cm)

df: Dilution factor

C: Enzyme concentration in solution (c mg/ml)

EXAMPLE 2

Preparation of Holo-Expressing Purified Enzyme 500 ml of Terrific Broth were transferred to a 2 L volumetric Sakaguchi flask followed by autoclaving for 20 minutes at 121° C., and adding separately aseptically filtered streptomycin to a concentration of 100 μg/ml. 5 ml of culturing liquid of *Pseudomonas putida* TE3493 (pNPG6-Q168A+L169P+A170M+E245D+M342I+A351T) precultured for 24 hours at 30° C. in PY medium containing 100 μg/ml of streptomycin were added to this medium followed by aerated agitation culturing for 40 hours at 30° C. The activity of PQQ dependent glucose dehydrogenase at completion of culturing was about 5 U/ml per ml of buffer as determined by the above-mentioned activity measurement.

After collecting the above-mentioned microorganisms by centrifugation and suspending in 20 mM phosphoric acid buffer (pH 7.0), the microorganisms were crushed by ultrasound treatment and further centrifuged to obtain a crude enzyme liquid in the form of the supernatant. The resulting crude enzyme liquid was separated and purified by HiTrap-SP (Amersham Bioscience) ion exchange column chromatography. Next, after dialyzing with 10 mM PIPES-NaOH buffer (pH 6.5), calcium chloride was added to a final concentration of 1 mM. Finally, the mixture was separated and purified by HiTrap-DEAE (Amersham Bioscience) ion exchange column chromatography to obtain the purified enzyme standard. The standard obtained by this method demonstrated a substantially single band in SDS-PAGE.

EXAMPLE 3

Confirmation of Substrate Specificity of Modified PQQGDH

The activity with respect to maltose of the purified modified PQQGDH produced in Example 2 was compared with wild type PQQGDH (Toyobo GLD-321). The respective activities were calculated for the case of using glucose for the substrate and using maltose for the substrate according to the method of Test Example 1 (with the exception that the substrate concentration in the assay mixture was made to be 4.8 mM), and the ratio of the activity value when using maltose to the activity value when using glucose was calculated and defined as maltose activity. As a result, in contrast to maltose activity of the wild type being 110%, maltose activity of the modified PQQGDH was only 13%, thereby confirming that an improvement in substrate specificity was achieved.

EXAMPLE 4

Production of Glucose Electrode Loaded with Modified PQQGDH 0.5 g of carbon graphite were placed in a mortar followed by the addition of 0.3 ml of liquid paraffin and kneading with a pestle for 30 minutes to produce a carbon paste. The resulting carbon paste was spread onto a platinum electrode followed by the addition of 10 μl of the modified PQQGDH solution (2,000 U/ml) produced in Example 2 and air drying for 30 minutes at room temperature. A cut cellulose semi-permeable membrane (molecular weight: 8,000) was placed over the dried enzyme electrode and the semi-permeable membrane was immobilized with plastic O-rings. The glucose electrode produced in this manner was then used after preliminarily immersing in the cold reaction solvent for 30 minutes.

EXAMPLE 5

Confirmation of Correlation Between Substrate Specificity and Solute in Glucose Measurement The substances listed in Table 1 were used as solutes, and buffers were respectively prepared having a final concentration of 50 mM (pH 5.5). Each of the solvents contained an activator/stabilizer in the form of calcium chloride at 1 mM and surfactant in the form of 0.1% Triton X-100 in addition to the solute listed in Table 1. Potassium ferricyanide was dissolved in each of the produced solvents to a concentration of 0.1 M to prepare reaction solutions. 20 ml of reaction solution were placed in a cuvette warmed to 25° C. followed by immersing the glucose electrode of Example 4 (working electrode), a counter electrode in the form of a platinum electrode, and a reference electrode in the form of an Ag/AgCl electrode therein and applying a voltage of +0.35 V. Glucose or maltose was added to a final concentration of 4 mM after the current value had become constant, and the current value that resulted in response to that addition was monitored. Maltose activity was calculated using the formula of maltose activity=B/A×100(%) by defining the current value that resulted in response to the addition of glucose as A, and defining the current value that resulted in response to the addition of maltose as B. The maltose activities when each of the solutes was added are shown in Table 1.

TABLE 1

Maltose Activity of Glucose Electrode When Using Various Solvents

| Solute | Maltose Activity (%) |
|---|---|
| MES | 29.6 |
| Phosphoric acid | 28.0 |
| Acetic acid | 35.5 |
| Citric acid | 23.4 |
| Succinic acid | 22.5 |
| Malonic acid | 23.2 |
| Phthalic acid | 4.9 |
| D,L-malic acid | 18.9 |
| Glutaric acid | 22.1 |
| 2-ketoglutaric acid | 19.3 |
| 3,3-dimethylglutaric acid | 14.9 |
| Adipic acid | 20.7 |
| Pimeric acid | 23.1 |
| Suberic acid | 20.2 |

Decreases in maltose activity were observed in the case of using dicarboxylic acid and tricarboxylic acid as compared with using the general-purpose buffer component, phosphoric acid, the Good's buffer, MES, and the monocarboxylic acid, acetic acid.

EXAMPLE 6

Confirmation of Effect of pH Conditions During Glucose Measurement on Substrate Specificity 50 mM phosphoric acid or pimeric acid solution containing 1 mM calcium chloride and 0.1% Triton X-100 (consisting of three types having pH values of 5.0, 6.0 and 7.0, respectively) were prepared. Maltose activity of the glucose electrode was investigated for each according to the method of Example 5. Those results are shown in Table 2.

TABLE 2

Maltose Activity of Glucose Electrode Under Various pH Conditions

| | pH | | |
|---|---|---|---|
| Solvent | 5.0 | 6.0 | 7.0 |
| Phosphoric acid | 23.7 | 36.8 | 50.8 |
| Pimeric acid | 15.2 | 23.8 | 49.1 |

As can be understood from these results, maltose activity was confirmed to decrease more in the case of using pimeric acid for the solute and lowering the pH. Based on the theory described in the present specification, it is surmised that similar results would be obtained even in the case of using other substances having two or more carboxyl groups in a molecule thereof.

EXAMPLE 7

(1) Confirmation of Substrate Specificity Using Glucose Assay System

Principle of Measurement

D-glucose+ferricyanide ion+PQQGDH D-glucono-1,5-lactone+ferrocyanide ion

Specificity to each substrate can be determined by changing D-glucose to other saccharides. The presence of the ferrocyanide ion produced by reduction of the ferricyanide ion was confirmed by measuring the decrease of absorbance at a wavelength of 420 nm by spectrophotometry.

(2) Method

Reagent

A. Buffers: Phthalic acid buffer: pH 7.0, 50 mM

Calcium phosphate buffer: pH 7.0, 50 mM

Glutaric acid buffer: pH 7.0, 50 mM

B. Potassium ferricyanide solution: 50 mM (0.165 g potassium ferricyanide (molecular weight: 329.25) dissolved in 10 ml of distilled water)

C. PQQGDH solution: 31000 U/ml (approx. 128 mg PQQGDH (Toyobo: GLD-331) dissolved in 5 ml of distilled water)

D. Substrate solution (D-glucose solution or maltose solution): 100 or 400 mM

Procedure

1. The following reaction mixture was prepared in a light shielding bottle, and stored on ice (prepared at use).

48.2 mL of each buffer solution (pH6.5) (A)

4.0 mL of potassium ferricyanide solution (B)

0.19 mL of (C)

2. 2.65 ml of the reaction mixture and 0.3 ml of additive were placed in a test tube (plastic) and pre-warmed for 5 minutes at 37° C.
3. 0.15 ml of substrate solution (D) were added and mixed gently.
4. The reduction in the absorbance relative to water at 420 nm was recorded for 1 to 3 minutes with a spectrophotometer while maintaining at a temperature of 37° C., and the ΔOD per minute was calculated from the initial linear portion of the curve (ΔOD test). At the same time, the same procedure was carried out with the exception of adding distilled water instead of glucose solution followed by measurement of the blank (ΔOD blank).

The above-mentioned procedure was carried out at each of the predetermined concentrations shown in Tables 1 to 3 using as additives succinic acid, adipic acid, suberic acid, pimeric acid, potassium chloride, ammonium chloride, diammonium hydrogen citrate, malonic acid, L-lysine, taurine, 3,3-dimethylglutaric acid, malic acid, glutaric acid, calcium glycerate, amino-n-butyric acid, sodium glycolate, sodium α-ketoglutarate, fumaric acid, glycerin, glutamic acid and serine. And the procedure was also carried out for those not containing additives to assess the effects of additives.

Calculation

Variation in absorbance per unit time was determined by calculating ΔOD/min(ΔOD test−ΔOD blank)

To evaluate whether activity had declined with respect to sugars other than glucose, the ΔOD/min (a) with D-glucose as the substrate solution and the ΔOD/min (b) with the other sugar in place of D-glucose as the substrate solution were measured, and the relative value ((b)/(a)×100) was calculated given 100 as the measurement value with glucose as the substrate.

The results of examining each of the additives based on phthalic acid buffer are shown in Table 1, the results of examining each of the additives based on potassium phosphate buffer are shown in Table 2, and the results of examining each of the additives based on glutaric acid buffer are shown in Table 3.

Activity with respect to maltose was able to be confirmed to decrease as a result of adding each of the additives described in Tables 3 to 5 regardless of the buffer composition.

Table 3 shows the relationship of the maltose activity lowering effects of modified PQQGDH in phthalic acid buffer (pH 7.0). Table 4 shows the relationship of the maltose activity lowering effects of modified PQQGDH in potassium phosphate buffer (pH 7.0). Table 5 shows the relationship of the maltose activity lowering effects of modified PQQGDH in glutaric acid buffer (pH 7.0).

In each of Tables 3 to 5, in the case the value of the ratio of measured values of maltose and glucose (maltose/glucose) relative to the control (control: no addition) is small, activity with respect to maltose during glucose measurement decreases.

A substrate concentration of 4.8 mM represents and a concentration of 86 mg/dl, and is equivalent to the blood sugar levels of healthy individuals. A substrate concentration of 1.92 mM represents a concentration of 350 mg/dl, and is considered to be the highest value of blood sugar levels among diabetics. Thus, efficacy of substrate specificity within a substrate concentration range of 4.8 to 19.2 mM has considerable significance for practical use.

Although activity with respect to maltose did not decrease in some cases (succinic acid, pimeric acid, diammonium hydrogen citrate and malonic acid) at a substrate concentration of 4.8 mM, activity was less than the control in all other cases.

TABLE 3

Phthalic Acid Buffer

| Reagent | Final Concentration (%) | Final Concentration (mM) | Maltose/glucose ratio 4.8 mM | Maltose/glucose ratio 19.2 mM |
|---|---|---|---|---|
| Control (reagent not added) | 0 | 0 | 0.72 | 0.75 |
| Succinic acid | 0.05 | 4.2 | 0.65 | 0.56 |
| | 0.1 | 8.5 | 0.73 | 0.57 |
| | 0.2 | 16.9 | 0.77 | 0.60 |
| Adipic acid | 0.05 | 3.4 | 0.66 | 0.68 |
| | 0.1 | 6.8 | 0.65 | 0.64 |
| | 0.2 | 13.7 | 0.65 | 0.58 |
| Suberic acid | 0.017 | 1.0 | 0.66 | 0.69 |
| | 0.033 | 1.9 | 0.67 | 0.62 |
| | 0.066 | 3.8 | 0.70 | 0.55 |
| Pimeric acid | 0.05 | 3.1 | 0.64 | 0.64 |
| | 0.1 | 6.2 | 0.71 | 0.58 |
| | 0.2 | 12.5 | 0.76 | 0.58 |
| Potassium chloride | 0.5 | 67.1 | 0.66 | 0.71 |
| | 1 | 134.1 | 0.67 | 0.64 |
| | 2 | 268.3 | 0.60 | 0.60 |
| Ammonium chloride | 0.5 | 93.5 | 0.60 | 0.67 |
| | 1 | 187.0 | 0.57 | 0.59 |
| | 2 | 373.9 | 0.52 | 0.52 |
| Diammonium hydrogen citrate | 0.5 | 22.1 | 0.79 | 0.55 |
| | 1 | 44.2 | 0.80 | 0.70 |
| | 2 | 88.4 | 0.89 | 0.63 |
| Malonic acid | 0.5 | 48.1 | 0.74 | 0.58 |
| | 1 | 96.1 | 0.77 | 0.57 |
| | 2 | 192.2 | 0.82 | 0.63 |
| L-lysine hydrochloride | 0.5 | 27.4 | 0.62 | 0.64 |
| | 1 | 54.8 | 0.61 | 0.58 |
| | 2 | 109.5 | 0.59 | 0.50 |
| Taurine | 0.5 | 40.0 | 0.71 | 0.72 |
| | 1 | 79.9 | 0.66 | 0.68 |
| | 2 | 119.9 | 0.62 | 0.68 |

TABLE 4

Potassium Phosphate Buffer

| Reagent | Final Concentration (%) | Final Concentration (mM) | Maltose/glucose ratio 4.8 mM | Maltose/glucose ratio 19.2 mM |
|---|---|---|---|---|
| Control (reagent not added) | 0 | 0 | 0.85 | 0.93 |
| Succinic acid | 0.5 | 42.3 | 0.65 | 0.84 |
| | 1 | 84.7 | 0.47 | 0.62 |
| | 2 | 169.4 | 0.34 | 0.45 |
| Ammonium chloride | 0.5 | 93.5 | 0.72 | 0.91 |
| | 1 | 187.0 | 0.58 | 0.84 |
| | 2 | 373.9 | 0.43 | 0.70 |
| Diammonium hydrogen citrate | 0.5 | 22.1 | 0.64 | 0.88 |
| | 1 | 44.2 | 0.52 | 0.76 |
| | 2 | 88.4 | 0.36 | 0.54 |
| Pimeric acid | 0.5 | 31.2 | 0.71 | 0.86 |
| | 1 | 62.4 | 0.58 | 0.80 |
| | 2 | 124.9 | 0.44 | 0.58 |
| 3,3-dimethylglutaric acid | 0.5 | 31.2 | 0.60 | 0.82 |
| | 1 | 62.4 | 0.44 | 0.64 |
| | 2 | 124.9 | 0.41 | 0.49 |
| L-lysine hydrochloride | 0.5 | 27.4 | 0.78 | 0.91 |
| | 1 | 54.8 | 0.71 | 0.93 |
| | 2 | 109.5 | 0.66 | 0.85 |

TABLE 5

Glutaric Acid Buffer

| Reagent | Final concentration (%) | Maltose/glucose ratio 4.8 mM | Maltose/glucose ratio 19.2 mM |
|---|---|---|---|
| Control (reagent not added) | 0 | 0.86 | 0.94 |
| DL-malic acid | 0.1 | 0.57 | 0.77 |
| | 1 | 0.34 | 0.40 |
| Glutaric acid | 0.1 | 0.65 | 0.81 |
| | 1 | 0.34 | 0.54 |
| Succinic acid | 0.1 | 0.55 | 0.75 |
| | 1 | 0.35 | 0.52 |
| Adipic acid | 0.1 | 0.73 | 0.84 |
| | 1 | 0.43 | 0.67 |
| Diammonium hydrogen citrate | 0.1 | 0.78 | 0.90 |
| | 1 | 0.59 | 0.82 |
| Suberic acid | 0.03 | 0.68 | 0.86 |
| | 0.33 | 0.38 | 0.49 |
| Pimeric acid | 0.1 | 0.63 | 0.78 |
| | 1 | 0.39 | 0.44 |
| 3,3-dimethylglutaric acid | 0.1 | 0.56 | 0.76 |
| | 1 | 0.37 | 0.47 |
| Calcium DL-glycerate | 0.33 | 0.60 | 0.82 |
| L-2-amino-n-butyric acid | 1 | 0.76 | 0.92 |
| sodium glycolate | 1 | 0.77 | 0.92 |
| Sodium α-ketoglutaric acid | 1 | 0.64 | 0.90 |
| Ammonium chloride | 1 | 0.56 | 0.71 |
| Fumaric acid | 1 | 0.68 | 0.88 |
| Malonic acid | 1 | 0.68 | 0.84 |
| Glycine | 1 | 0.76 | 0.93 |
| D-glutamic acid | 0.10 | 0.73 | 0.89 |
| L-serine | 1 | 0.73 | 0.87 |
| L-lysine hydrochloride | 1 | 0.65 | 0.87 |
| Taurine | 1 | 0.75 | 0.81 |

In this manner, among those modified forms in which substrate specificity with respect to glucose improved, substrate specificity was clearly determined to be further improved by about 1.1 to 2.5 times by modifying the reaction liquid composition even in the case of buffers in the neutral range.

The improvement of substrate specificity according to the present is able to improve the accuracy of glucose assay reagents, glucose assay kits and glucose sensors.

According to the present invention, a composition for measuring glucose or a method for measuring glucose can be obtained that has improved substrate specificity. This composition or method for measuring glucose can be used in a glucose assay kit or glucose sensor having improved measurement accuracy.

---

What is claimed is:

1. A method for lowering a reactivity on maltose in glucose measurement comprising a step of reacting modified pyrroloquinoline quinone dependent glucose dehydrogenase in the presence of at least one substance selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid, wherein the modified pyrroloquinoline quinone dependent glucose dehydrogenase consists of SEQ ID NO: 1 except that position 168 of SEQ ID NO: 1 and at least one position selected from the group consisting of positions 169, 170, 245, 342, and 351 of SEQ ID NO: 1 are substituted with another amino acid, and wherein a pH of 5.0 to 6.0 is maintained during the glucose measurement reaction.

2. The method according to claim 1, wherein the at least one substance is selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid and citric acid.

3. The method according to claim 1, wherein the at least one substance is selected from the group consisting of succinic acid, adipic acid, suberic acid, pimeric acid, potassium chloride, ammonium chloride, diammonium hydrogen citrate, malonic acid, L-lysine, taurine, 3,3-dimethylglutaric acid, malic acid, glutaric acid, calcium glycerate, amino-n-butyric acid, sodium glycolate, sodium α-ketoglutarate, fumaric acid, glycine, glutamic acid and serine.

4. The method for lowering a reactivity on maltose in the measurement of glucose according to claim 1, wherein the total added amount of at least one substance selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid is 0.05% or more as a percent by weight in solution.

5. The method according to claim 1, wherein the reaction is carried out in the presence of at least one mediator.

6. The method according to claim 5, wherein the mediator is a ferricyanide salt.

7. The method according to claim 1, wherein the modified pyrroloquinoline quinone dependent glucose dehydrogenase has a lowered reactivity on maltose as compared with an enzyme having SEQ ID NO: 1.

8. A composition for measuring glucose comprising (a) a modified pyrroloquinoline quinone dependent glucose dehydrogenase consisting of SEQ ID NO: 1 except that position 168 of SEQ ID NO: 1 and at least one position selected from the group consisting of positions 169, 170, 245, 342, and 351 of SEQ ID NO: 1 are substituted with another amino acid, and (b) one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

9. A glucose sensor comprising (a) a modified pyrroloquinoline quinone dependent glucose dehydrogenase consisting of SEQ ID NO: 1 except that position 168 of SEQ ID NO: 1 and at least one position selected from the group consisting of positions 169, 170, 245, 342, and 351 of SEQ ID NO: 1 are substituted with another amino acid, and (b) one or more substances selected from the group consisting of succinic acid, malonic acid, glutaric acid, malic acid, phthalic acid, 2-ketoglutaric acid, 3,3-dimethylglutaric acid, pimeric acid, suberic acid, adipic acid, maleic acid, potassium chloride, ammonium chloride, diammonium hydrogen citrate, L-lysine, taurine, calcium glycerate, amino-n-butyric acid, sodium glycolate, sodium α-ketoglutarate, fumaric acid, glycine, glutamic acid, serine and citric acid.

10. A kit for measuring glucose comprising the composition of claim 8.

11. A method for measuring glucose comprising using the glucose sensor of claim 9, to measure glucose of a sample.

* * * * *

SEQUENCE LISTING

```
<160> NUMBER OF SEQ ID NOS: 2

<210> SEQ ID NO 1
<211> LENGTH: 455
<212> TYPE: PRT
<213> ORGANISM: Acinetobacter baumannii

<400> SEQUENCE: 1

Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Val Ser Gly Ser Ala Lys Thr Val Phe
    50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Ser Lys Asp Tyr
            180                 185                 190

His Thr Tyr Met Gly Lys Val Leu Arg Leu Asn Leu Asp Gly Ser Val
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

Val Leu Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Thr Asn Lys
        275                 280                 285

Ser Gln Ile Lys Asp Leu Ala Gln Asn Gly Ile Lys Val Ala Thr Gly
    290                 295                 300

Val Pro Val Thr Lys Glu Ser Glu Trp Thr Gly Lys Asn Phe Val Pro
```

-continued

```
305                 310                 315                 320

Pro Leu Lys Thr Leu Tyr Thr Val Gln Asp Thr Tyr Asn Tyr Asn Asp
                325                 330                 335

Pro Thr Cys Gly Glu Met Ala Tyr Ile Cys Trp Pro Thr Val Ala Pro
            340                 345                 350

Ser Ser Ala Tyr Val Tyr Thr Gly Gly Lys Lys Ala Ile Pro Gly Trp
        355                 360                 365

Glu Asn Thr Leu Leu Val Pro Ser Leu Lys Arg Gly Val Ile Phe Arg
    370                 375                 380

Ile Lys Leu Asp Pro Thr Tyr Ser Thr Thr Leu Asp Asp Ala Ile Pro
385                 390                 395                 400

Met Phe Lys Ser Asn Asn Arg Tyr Arg Asp Val Ile Ala Ser Pro Glu
                405                 410                 415

Gly Asn Thr Leu Tyr Val Leu Thr Asp Thr Ala Gly Asn Val Gln Lys
            420                 425                 430

Asp Asp Gly Ser Val Thr His Thr Leu Glu Asn Pro Gly Ser Leu Ile
        435                 440                 445

Lys Phe Thr Tyr Asn Gly Lys
    450                 455


<210> SEQ ID NO 2
<211> LENGTH: 1368
<212> TYPE: DNA
<213> ORGANISM: Acinetobacter baumannii

<400> SEQUENCE: 2

gatatacctc tgacacctgc tcagttcgca aaagcgaaaa cagaaaattt tgataaaaaa     60

gtgattctgt ccaatttaaa taaaccacat gctttgttat gggggccaga taatcaaatt    120

tggttaaccg aacgtgcaac tggcaaaatt ttaagagtaa atcctgtatc tggtagcgcg    180

aaaacagtat ttcaggttcc tgaaattgtg agtgatgctg atgggcaaaa tggtttgtta    240

ggttttgctt ttcatcctga ctttaaacat aacccttata tctatatttc aggcactttt    300

aaaaatccaa aatctacaga taaagagtta cctaatcaga cgattattcg tagatatacc    360

tataataaaa ctacagatac atttgaaaag cctattgatt tgattgcagg tttaccgtca    420

tcaaaagatc atcagtctgg tcgtctcgtt attggtccag accaaaaaat ctactatacg    480

attggtgacc aaggtcgtaa tcagttagct tatctgttct taccgaatca ggcacagcat    540

actccgactc agcaagagct caatagtaaa gactaccata catatatggg taaagtatta    600

cgcttaaatc tggacggcag tgtacctaaa gacaacccaa gctttaacgg cgtagtgagt    660

catatctaca ctttagggca ccgtaatcca caaggtttag catttgcccc aaatggaaag    720

cttttacaat ctgagcaagg accaaattct gatgatgaaa ttaaccttgt attaaaaggt    780

ggtaactatg gctggccaaa tgtagctggt tataaagatg acagtggtta tgcctatgca    840

aactattcgg cagcaaccaa taaatcacaa attaaagatt tagctcaaaa cgggataaaa    900

gtagcaacag gtgttcctgt gactaaagag tctgaatgga ctggtaaaaa ctttgtgccg    960

cctttgaaaa ctttatatac ggtacaagat acctataact ataatgaccc tacttgtggt   1020

gagatggcat atatttgctg gccaacggtt gcaccgtcat cagcatatgt atatacggga   1080

ggcaaaaaag cgattccagg gtgggaaaat acattattgg tcccatcttt aaaacgtggg   1140

gtgattttcc gtattaaatt ggacccgaca tatagcacga ctttggatga tgctatccca   1200

atgtttaaaa gcaataaccg ttatcgtgat gtcatcgcta gtccagaagg taatacctta   1260
```

-continued

```
tatgtgctga ctgatacagc ggggaatgta caaaaagatg atggttctgt cactcatact   1320

ttagagaatc ccggttctct cattaaattt acatataacg gtaagtaa                1368
```